United States Patent [19]

Bergstein et al.

[11] Patent Number: 4,988,827
[45] Date of Patent: Jan. 29, 1991

[54] ETHER ISONITRILES AND RADIOLABELED COMPLEXES THEREOF

[75] Inventors: Paul L. Bergstein, Norwood, Mass.; Vinayakam Subramanyam, Wilmington, Del.

[73] Assignee: E.I. Du Pont de Nemours and Company, Wilmington, Del.

[21] Appl. No.: 56,003

[22] Filed: Jun. 1, 1987

Related U.S. Application Data

[63] Continuation-in-part of Ser. No. 925,091, Nov. 5, 1986, abandoned, which is a continuation-in-part of Ser. No. 812,470, Dec. 23, 1985, abandoned.

[51] Int. Cl.$^5$ ............... C07D 317/00; C07C 265/00
[52] U.S. Cl. .................................. 549/451; 558/302; 549/371; 549/347; 549/373; 549/377; 549/449; 424/1.1
[58] Field of Search .............. 558/302; 549/451, 371, 549/373, 377, 449, 347

[56] References Cited

U.S. PATENT DOCUMENTS

| | | | |
|---|---|---|---|
| 3,419,596 | 12/1968 | Fetzer et al. | 558/302 |
| 3,661,965 | 5/1974 | Arlt et al. | 260/464 |
| 3,794,674 | 2/1974 | Hoffmann et al. | 260/465 B |
| 4,452,774 | 6/1984 | Jones et al. | 424/1.1 |
| 4,686,302 | 8/1987 | Merger et al. | 558/314 |
| 4,735,793 | 4/1988 | Jones et al. | 424/1.1 |

FOREIGN PATENT DOCUMENTS 0144885 6/1985 European Pat. Off. .
8303761 11/1988 PCT Int'l Appl. .

OTHER PUBLICATIONS

Schollkopf, Ulrich, et al., "Syntheses with Alpha-Metalated Isocyanides", Org Chem, Justus L. Ann. Chem (11) 2105-21, 1976.
Navolokina et al., "Production of Unsymmetrical Ethers . . . ," J. Org. Chem. USSR, 1980, 16, pp. 1382-1386.
C.A. 79:42427f (Schoellkopf et al.)—Abstract.
C.A. 87:135255d (Schoellkopf et al.)—Abstract.
Tetrahedron Letters, vol. 26, No. 28, 1985, pp. 3291-3294, Loewe et al.
Bulletin of the Chemical Society of Japan, vol. 52, No. 7, July, 1979, pp. 1975-1977, Watanabe et al.

Primary Examiner—John S. Maples

[57] ABSTRACT

Ether-substituted isonitriles, Tc99m complexes thereof, and processes for myocardial tissue radioimaging using the Tc99m complexes.

26 Claims, No Drawings

ETHER ISONITRILES AND RADIOLABELED COMPLEXES THEREOF

FIELD OF THE INVENTION

This invention relates to novel ether-substituted isonitriles, radiolabeled complexes of these isonitriles, and methods of using the radiolabeled complexes for myocardial imaging.

BACKGROUND OF THE INVENTION

Isonitrile complexes of various radionuclides and their use as imaging agents have been described by Jones et al, U.S. Pat. No. 4,452,774 issued June 5, 1984. The complexes described by Jones, et al are of the general formula:

$$[A((CN)_xR)_yB_zB'_{z'}]^n$$

in which A is a radionuclide selected from radioactive isotopes of Tc, Ru, Co, Pt, Fe, Os, Ir, W, Re, Cr, Mo, Mn, Ni, Rh, Pd, Nb, and Ta, for example, $^{99m}$Tc, $^{99}$Tc, $^{97}$Ru, $^{51}$Cr, $^{57}$Co, $^{188}$Re and $^{191}$Os; $(CN)_xR$ is a monodentate or polydentate isonitrile ligand bonded to the radionuclide through the carbon atom of the CN group; R is an organic radical; B and B' are independently selected from other ligands well known to those skilled in the art that result in isonitrile complexes, including solvents such as water, chloro and bromo groups, and ligands comprising one or more neutral donor atoms capable of forming bonds with said radionuclide; x and y are each independently integers from 1 to 8; z and z' are each independently 0 or an integer from 1 to 7; with the proviso that $(xy)+z+z'$ is less than or equal to 8; and n indicates the charge of the complex and can be 0 (neutral), or a positive or negative integer the value of which depends upon the valence state of A, and the charges on R, B and B'. Any desired counterion can be present as required by the charge on the complex with the proviso that such counterion must be pharmaceutically acceptable if the complex is to be used in vivo.

In the above formula, R is an organic radical that can be aliphatic or aromatic and may be substituted with a variety of groups which may or may not be charged. When the organic radical R carries a charged substituent group, the charge on the resultant complex is the summation of the charges of the ligands (R, B and B') and the charge of the radionuclide. Among the aromatic R groups which may be present are phenyl, tolyl, xylyl, naphthyl, diphenyl and substituted aromatic groups containing such substituents as halo, e.g., chloro, bromo, iodo or fluoro; hydroxy, nitro, alkyl, alkoxy, etc.; among the aliphatic R groups which may be present are alkyl, preferably containing 1 to 20 carbon atoms, such as methyl, ethyl, n-propyl, isopropyl, n-butyl, isobutyl, n-hexyl, 2-ethylhexyl, dodecyl, stearyl, etc. Substituent groups may also be present in the aliphatic groups, including among others the same substituent groups as those listed above for aromatic groups.

The complexes described by Jones et al. are described as being useful for visualizing cardiac tissue, detecting the presence of thrombi in the lung and associated areas of blood perfusion deficits, studying lung function, studying renal excretion, and imaging bone marrow and the hepatobiliary system.

In practice, the technetium complex of the simple hydrocarbon isonitriles such as t-butylisonitrile preferred by Jones et al. have demonstrated somewhat high concentration in the lung and liver in humans. [Holman, et al., *J. Nucl. Med.*, 25, 1380(1984)]. The high early concentration of radionuclide in the lung has required that imaging of the heart be delayed to allow the lung activity to clear before useful myocardial images can be obtained. In addition, the high concentration of radionuclide in the liver has made the detection of perfusion defects in the apical region of the myocardium more difficult. Clearly, the need exists for a more selective agent for myocardial imaging.

SUMMARY OF THE INVENTION

The subject invention provides novel ether-substituted isonitriles and diagnostic kits thereof. radiolabeled complexes of these isonitriles (preferably Tc99m), and diagnostic methods utilizing the radiolabeled complexes. Although the general formula disclosed in Jones et al. U.S. Pat. No. 4,452,774 encompasses the radiolabeled, mono ether-substituted isonitrile complexes of this invention, such complexes are not specifically disclosed, and the superior imaging characteristics of these ether-substituted isonitriles are not contemplated by Jones et al.

More specifically, one aspect of this invention provides novel ether-substituted isonitriles (and kits thereof) of the formula:

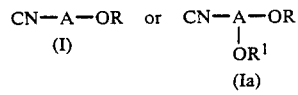

wherein
A is a straight or branched chain alkyl group, and
R and R$^1$ each independently is a straight or branched chain alkyl group or taken together are a straight or branched chain alkylene group, provided that (1) the total number of carbon atoms in A plus R in formula (I) is 4 to 6, provided further that when the total number of carbon atoms is 6, then the carbon atom alpha to the isonitrile group is a quaternary carbon, and still further provided that A is not $(CH_2)_3$, and (2) the total number of carbon atoms in A plus R plus R$^1$ in formula (Ia) is 4 to 9.

Another aspect of this invention relates to novel radiolabeled complexes of these ether isonitriles of the general formula

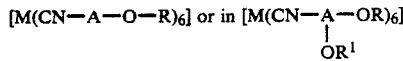

where M is a radionuclide, most preferably Tc99M, particularly 99mTc(I). Another aspect of this invention relates to the use of these radio-labeled isonitrile complexes as myocardial imaging agents.

DETAILED DESCRIPTION OF THE INVENTION

Isonitriles of the present invention can be readily prepared by formylation of an alkoxyamine of the general formula II or IIa to give the corresponding formamide III or IIIa, followed by dehydration to the isonitrile I or Ia as shown below:

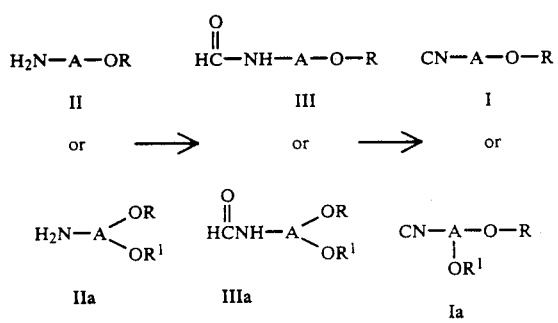

A variety of methods for the formylation and dehydration reactions are available in the literature and are well known to one skilled in the art of organic synthesis.

The amines II can be prepared by a variety of methods known to one skilled in the art. In particular, the amines can be prepared by opening of an aziridine IV with an alcohol in the presence of an acid catalyst to give a mixture of the two amines V and VI which can be separated by distillation.

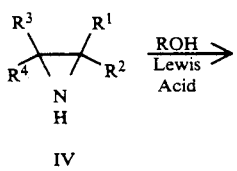

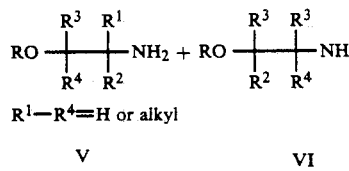

Alternatively, the amines can be prepared from alkoxyesters VII wherein A' is a hydrocarbon of 2 or 3 carbon atoms. Formation of the amide VIII by reaction with ammonia or ammonium hydroxide, followed by reduction with lithium aluminum hydride or another reducing agent known to reduce amides affords the amine IX.

RO—A'—CO$_2$R$^3$ $\xrightarrow{NH_4OH}$

VII

RO—A'—CONH$_2$ $\xrightarrow{LiAlH_4}$ RO—A'—CH$_2$NH$_2$

VIII            IX

The amines II can also be prepared from the alkoxyesters X. Formation of the amide XI proceeds as described above. The amide XI is subjected to the Hofmann Rearrangement to provide the amine II.

RO—A—CO$_2$R$^5$ ⟶ RO—ACONH$_2$ $\xrightarrow[-OH]{Br_2}$

X            XI

RO—A—NH$_2$

II

Alternatively, the mono ether isonitriles can be prepared from amino alcohols XII by first reacting with a formylating agent, such as ethyl formate or formic acetic anhydride, to form the formamide-formate XIII. Conversion of the formamide-formate to the isonitrile-formate XIV is accomplished as already described for the other formamides. Mild aqueous hydrolysis of the formate yields the isonitrile-alcohol XV which can then be alkylated under standard alkylation conditions such as using sodium hydride and methyl halide such as iodide.

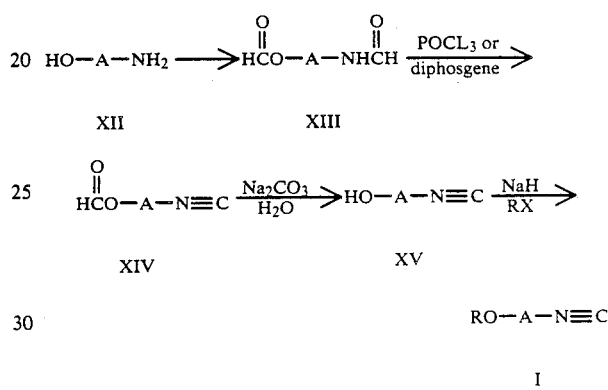

RO—A—N≡C

I

In cases where the amines of formula IIa (dialkoxyamines) are ketals, they can be prepared by (a) converting an amino acid XVI to an acetamide ketone XVII by reaction with an acid anhydride (such as acetic anhydride) and pyridine (in a boiling water bath), (b) hydrolyzing the amido ketone by refluxing in an aqueous solution of a hydrohalic acid to an amino ketone hydrohalide XVIII, and then (c) converting the hydrohalide to an amino diether of formula IIa by reaction with an alcohol (such as methanol or ethanol or a diol (such as ethylene glycol or propylene glycol). This reaction sequence is shown below.

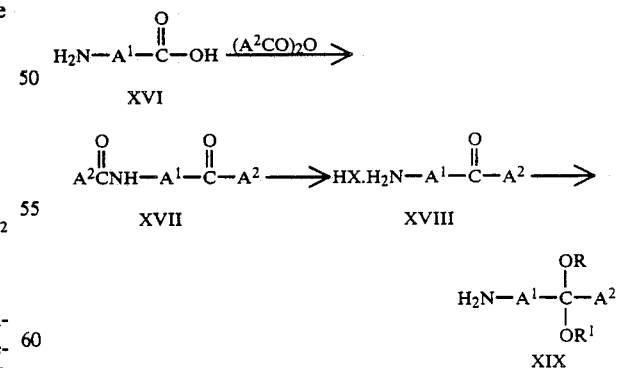

where A$^1$ and A$^2$ are chosen such that A$^1$—C—A$^2$ fulfills the requirements of A as specified for structure Ia.

Alternatively, formamides of formula IIIa can be prepared by reacting an aminodiol XX with ethyl formate or formic acetic anhydride to form a formamidodiol XXI, which is then converted to a formamido diether IIIa by reaction with acetone, formaldehyde or an equivalent such as 2,2-dimethoxy propane. This reaction sequence is shown below:

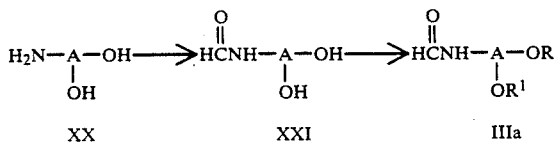

Mono ether-substituted isonitriles useful in the practice of this invention include:

| | |
|---|---|
| CNCH₂CH₂CH₂OCH₃; | CNCH₂CH₂CH₂OCH₂CH₃ |
| CNC(CH₃)₂OCH₂CH₃; | CNC(CH₃)₂OCH₃; |
| CNCH₂C(CH₃)₂OCH₃; | CNC(CH₃)₂CH₂OCH₃; |
| CNCH(CH₃)CH₂OCH₃; | CNCH(CH₃)CH₂OCH₂CH₃; |
| CNCH₂CH(CH₃)OCH₃; | CNCH₂CH(CH₃)OCH₂CH₃; |
| CNCH(CH₃)CH(CH₃)OCH₃; | CNCH₂CH(CH₃)CH₂OCH₃; |
| CNCH₂CH(CH₃)OCH₃; | CNCH₂CH(CH₃)₂; |
| CNCH₂CH₂OCH₂CH₃; | CNCH(CH₃)OCH(CH₃)₂; |
| CNCH₂CH(CH₂CH₃)OCH₃; | CNCH(CH₂CH₃)CH₂OCH₃; |
| CNCH(CH₃)CH₂CH₂OCH₃; | CNC(CH₃)₂CH₂CH₂OCH₃. |

Specific examples of the preparation of mono ether-substituted isonitriles are detailed below.

Preparation 1: Synthesis of
1-methoxy-2-methylpropyl-2-amine and
2-methoxy-2-methylpropyl-1-amine A. Synthesis of 2,2-Dimethylaziridine 2-Amino-2-methyl-1-propanol (100 g, 1.12 mol) was dissolved in water (200 ml), and placed in a 1000 ml round-bottomed flask. Concentrated sulfuric acid (100 g, 1.12 mol) was dissolved in water (200 ml) and was added to the amine solution. The resulting warm solution was distilled at atmospheric pressure. The temperature rose to 120° C., the pressure was reduced to aspirator pressure (approximately 25 mm Hg) and the distillation continued until the temperature of the distillate reached 150° C. The resulting brown gum was placed under vacuum (approximately 1 mm Hg) and heated to 170°–200° C. for 1.5 hours. Some charring occurred, and a solid resulted. The flask was then broken while encased in a protective pad, and the glass discarded. The solid was broken up using a hammer, and then a mortar and pestle, until it was mostly a fine powder and no pieces were larger than ¼ in diameter. The solid was added to a solution containing sodium hydroxide (100 g, 2.5 mol) in water (150 ml). The suspension was heated to 110° C. using a salt water bath and the solid slowly dissolved to form a black solution. The product distilled from this solution at 70°–88° C. onto sodium hydroxide pellets (25 g, 0.63 mol). By the end of the distillation a white precipitate had formed in the pot. After filtration through glass wool, the water layer was removed and the product was dried over sodium hydroxide, filtered, and dried over sodium metal. The product was distilled from sodium metal at 70°–73° C. to yield 46.2 g of a clear, colorless product (yield 58%).

NMR (CHCl₃): δ 0.1 (s. 1H, NH), 1.25 (s, 6H, CH₃). 1.55 (s, 2H, CH₂)

B. Synthesis of 1-methoxy-2-methylpropyl-2-amine and 2-methoxy-2-methylpropyl-1-amine 2.2-Dimethylaziridine (27.68 g 0.39 mol) was dissolved in freshly distilled methanol (50 g). This was cooled to −10° C. in an ice/acetone bath. Boron-trifluoride bis-methanol complex (58.32 g, 0.44 mol) was dissolved in freshly distilled methanol (50 ml) and cooled in an ice/acetone bath to −10° C. The cooled borontrifluoride solution was slowly added to the cooled aziridine solution over a 20 minute time period. The resulting solution was allowed to slowly warm to room temperature. The solution was stirred at room temperature for seven days while the production of the product was monitored by NMR. The solution was reduced in volume using rotary evaporation (25 mm Hg, 40° C.) to approximately one-half original volume. Sodium methoxide in methanol (95.04 g of a 25% w/w solution, 0.594 mol) was added and a white precipitate formed. Diethylether (300 ml) was added and the precipitate was filtered. The still cloudy solution was distilled, and when the temperature reached 60° C., it was filtered again. The distillation was continued and a mixture of the two amines was obtained (14.24 g, 35%). The two amines were separated using careful fractional distillations to yield pure 2-methoxy-2-methylpropyl-1-amine (b.p. 123°–124° C., NMR (CDCl₃): δ 1.2 (s, 8H, NH₂CH₃), 2.7 (s, 2H, CH₂), 3.3 (s, 3H, CH₃O) and 1-methoxy-2-methylpropyl-2-amine (b.p. 103°–104° C.), NMR (CDCl₃), δ 1.1 (s, 6H, CH₃), 1.6 (bs, b 2H, NH₂), 3.1 (s, 2H, CH₂), 3.4 (s, 3H, CH₃O).

Preparation 2: Synthesis of
2-methoxy-2-methylpropyl-1-amine

A. Synthesis of Methyl 2-methoxy-2-methylpropanoate

Dimethyl formamide (100 ml) and tetrahydrofuran (300 ml) were placed in a 1000 ml three-neck round-bottom flask equipped with a thermometer, a mechanical stirrer, and a dropping funnel. An 80% dispersion of sodium hydride in oil (19.80 g, 0.66 mol) was added to form a gray suspension. The suspension was cooled in an ice-water bath. Methyl hydroxyisobutyrate (70.8 g, 0.60 mol) was dissolved in tetrahydrofuran (50 ml) and added slowly to the cooled sodium hydride suspension while the temperature was held below 15° C. The resulting suspension was stirred for one hour. Methyl iodide (freshly distilled, 108.75 g, 0.75 mol) in tetrahydrofuran (25 ml) was slowly added to the cooled suspension. The addition took 1.5 hours, during which the temperature was held below 15° C. The suspension was stirred and allowed to warm to room temperature for 15 hours. The suspension was poured into ethyl acetate (300 ml) and water (300 ml). The clear layers were separated and the aqueous phase was extracted with ethyl acetate (300 ml). The combined organic layers were decolorized with water (200 ml) containing sodium bisulfite (10 g). The organic phase was separated and dried over magnesium sulfate. The solvent was mostly removed by rotary evaporation (25 mm Hg, 30° C.). The resulting solution was distilled at atmospheric pressure and the product collected at 137°–146° C. The product was contaminated with DMF, but by NMR the yield of product was 48.8 g (61%).

NMR (CHCl₃) δ 1.4 (s, 6H, CH₃), 3.3 (s. 3H, CH₃O ether), 3.8 (s, 3H, CH₃O ester).

B. Synthesis of 2-methoxy-2-methylpropanamide

Methyl 2-methoxy-2-methylpropanoate (42.24 g, 32 mol, this had with it 10.6 g of DMF) was added to ammonium hydroxide (200 ml). This resulted in a two-phase system that was stirred at 25°–30° C. for 17 hours. The clear homogeneous solution that resulted was concentrated to a white precipitate by rotary evaporation (25 mm Hg, 50° C.). The wet solid was dissolved in methylene chloride (200 ml). The water layer was separated and the methylene chloride layer passed through a plug of silica. The water layer was washed with methylene chloride (100 ml) and this methylene chloride layer was also passed through the plug of silica. Finally, methylene chloride (100 ml) was passed through the silica plug and the combined methylene chloride fractions were evaporated by rotary evaporation (25 mm Hg, 35° C.) to give a white crystalline material. This was dried in vacuo to yield 29.5 g (79%).

NMR (CDCl$_3$) δ 1.4 (s. 6H, CH$_3$), 3.3 (9, 3H, CH$_3$O), 6.4 (very b, 2H, NH$_2$)

C. Synthesis of 2-methoxy-2-methylpropyl-1-amine

Lithium aluminum hydride (3.04 g. 0.08 mol) was added to a 250 ml dry two-neck round-bottom flask. The flask was kept under dry nitrogen at all times. Dry tetrahydrofuran (THF) (25 ml) was added and the suspension stirred. 2-Methoxy-2-methylpropanamide (8.19 g, 0.07 mol) was dissolved in 80 ml dry tetrahydrofuran and added slowly to the lithium aluminum hydride suspension. The addition was just fast enough to maintain a gentle reflux. The addition took one-half hour and the resulting suspension was refluxed for an additional hour. The suspension was allowed to cool. 3 ml water was added dropwise with stirring, followed by 3 ml of 15% sodium hydroxide. Finally. 9 ml water was added and the warm suspension was stirred for 15 minutes. The white precipitate was filtered on a medium frit and washed repeatedly with THF. The combined THF fractions were distilled at atmospheric pressure. The THF was removed below 70° C. The product distilled at approximately 124° C.

Yield: 4.19 g (58%)

NMR (CDCl$_3$) δ 1.15 (s, 8H, CH$_3$, NH$_2$), 2.6 (s, 2H, CH$_2$), 3.2 (s, 3H, CH$_3$O).

Preparation 3: Synthesis of N-(2-methoxy-2-methylpropyl) formamide

Formic acid (19.2 g, 0.40 mol) and acetic anhydride (40.8 g, 0.40 mol) Were combined and heated to 45°-50° C. for one hour and cooled to approximately 0° C. in an ice/acetone bath. A solution of 2-methoxy-2-methylpropyl-1-amine (36 g, 0.35 mol), precooled to approximately 0° C. in an ice/acetone bath was added slowly while keeping the temperature of the mixture below 12° C. After the addition was complete, the mixture was allowed to warm slowly to room temperature and was stirred at room temperature overnight. The solution was evaporated and the residue distilled at 97°-107° C./1-2 mm Hg. to give 43.2 g (94%).

NMR (CDCl$_3$): δ 1.2 (s, 6H, CH$_3$), 3.3 (m, 5H, CH$_3$O and CH$_2$), 6.6 (b, 1H, NH), 8.2 (bs, 1H, HCO).

Preparation 4: N-[2-(1-methoxypropyl)]formamide

Formic acid (16.80 g. 0.35 mol) and acetic anhydride (37.50 g. 0.35 mol) were combined and heated at 45°-50° C. for 1 hour and cooled to approximately 0° C. in an ice/acetone bath. 2-amino-1-methoxy propane (26.7 g, 0.30 mol) was cooled in an ice/acetone bath to below 0° C. Formic acid (25 ml) was slowly added to the cooled amine. The resulting solution was cooled further until it was below 0° C. The amine solution was added to the cooled formic-acetic anhydride solution and the resulting solution was stirred and allowed to slowly warm to room temperature overnight. The solutions was distilled under low pressure (~1 mm Hg) and the formic acid, acetic acid, and formic-acetic anhydride all distilled at low temperature. The product was distilled at 79°-85° C. to yield a clear, colorless oil. Yield 33.13 g, (94%).

NMR (CHCl$_3$) δ 1.05 (d 3H, CH$_3$—C), 3.4 (M, 5H, CH$_3$O)CH$_2$O 4.2 (m. 1H, CH), 6.8 (b, 1H, N-H), 8.0 (b, 1H, HC=O).

Isonitrile Synthesis

The following synthetic routes for preparation of 2 methoxy-2 methylpropyl-1-isonitrile, 1-methoxypropyl-2-isonitrile, and 3-isonitrile-3-methyl-1-methoxybutane are also useful for the preparation of the other corresponding isonitrile versions of the mono ether compounds detailed above.

EXAMPLE 1

Preparation of 2-methoxy-2-methylpropyl-1-isonitrile

N-(2-methoxy-2-methylpropyl)formamide (1.97 g. 0.015 mol) was added to methylene chloride (23 ml). Triethylamine (4.04 g, 0.040 mol) was added and the clear solution was cooled in an ice/water bath. Diphosgene (trichloromethyl chloroformate, 1.68 g, 0.0085 mol) was dissolved in methylene chloride (10 ml) and slowly added to the cooled formamide solution (45 minutes). The suspension was allowed to warm to room temperature with stirring for two hours. The suspension was then poured into water (25 ml) containing sodium dihydrogen phosphate (6.90 g, 0.05 mol). The methylene chloride layer was separated and dried over sodium carbonate. The solution was then distilled under reduced pressure (25 mm Hg), product distilled at 56°-59° C., 0.530 g (31% yield).

NMR (CDCl$_3$) δ 1.3 (s. 6H, CH$_3$), 3.25 (s, 3H, CH$_3$O), 3.4 (m, 2H, CH$_2$).

EXAMPLE 2

Preparation of 1-methoxypropyl-2-isonitrile

N-[2-(1-methoxypropyl)]formamide (11.7 g, 0.10 mol) was dissolved in methylene chloride (125 ml). Triethylamine (30.30 g. 0.30 mol) was added and the clear solution was cooled in an ice/water bath. Diphosgene (11.88 g, 0.06 mol) was dissolved in methylene chloride (40 ml). The diphosgene solution was added slowly to the cooled formamide solution. The resulting suspension was stirred and allowed to slowly warm to room temperature for 1.5 hours. The suspension was poured into water containing sodium carbonate (42.4 g. 0.40 mol). The methylene chloride layer was separated and washed with water containing sodium dihydrogen phosphate (55.2 g 0.40 mol). The methylene chloride layer was separated and dried over sodium carbonate (anhydrous).

The solution was filtered and distilled at aspirator pressure (~25 mm Hg). The product distilled at 63°-66° C. Yield 5.83 g (58.8%).

NMR (CDCl$_3$) δ 1.05 (6 equivalent peaks, 3H, CH$_3$C), 3.0 (s, 3H, CH$_3$O), 3.1 (m, 2H, CH$_2$), 3.5 (m, 1H, CH).

EXAMPLE 3

Synthesis of 3-isonitrilo-3-methyl-1-methoxybutane

A. Synthesis of 3-formamido-3-methyl-1-butanol

3-Amino-3-methyl-1-butanol (20.60 g, 0.20 mol) was added to ethyl formate (29.60 g, 0.40 mol), and the resulting clear solution was heated to reflux under nitrogen for 2 hours, and then allowed to cool to room temperature. The ethyl formate and ethanol by-product were removed by rotary evaporation (35° C., 25 Torr). The resulting oil was dried under vacuum (25° C., 0.1 Torr) to yield 25.86 g (99%).

NMR (CDCl$_3$) 1.4 (d, 6H, CH$_3$), 2.0 (m, 2H), C—CH$_2$), 3.9 (m. 2H, O—CH$_2$). 7.1 (bs, 1H, NH), (m. 1H, HCO).

B. Synthesis of 3-formamido-3-methyl-1-butyl formate

Formic acid (6.90 g, 0.15 mol) was added to acetic anhydride (15.30 g, 0.15 mol) and warmed to 45°–50° C. for one hour on a water bath. The resulting solution was cooled to below 0° C. in an ice/acetone bath. 3-Formamido-3-methyl-1-butanol (13.10 g, 0.10 mol) was added and the solution allowed to slowly warm to room temperature with stirring (16 hours). The solution was distilled under vacuum (1 Torr, 105°–110° C.) to yield 12.43 g (78%).

NMR (CDCl$_3$): 1.4 (s, 6H, CH$_3$), 2.1 (t, 2H, C—CH$_2$), 4.2 (t, 2H, O—CH$_2$), 6.0 (bs, 1H, NH). 8.0 (m, 2H, HCOO).

C. Synthesis of 3-isonitrilo-3-methyl-1-butyl formate

3-Formamido-3-methyl-1-butyl formate (11.13 g, 0.07 mol) and triethylamine (21.21 g, 0.21 mol) were dissolved in methylene chloride (350 ml). The resulting solution was cooled in an ice/water bath under nitrogen. Trichloromethyl chloroformate (diphosgene) (8.32 g, 0.042 mol) was dissolved in methylene chloride (50 ml) and added dropwise to the stirred, cooled formamide solution over 30 minutes. The resulting suspension was stirred and allowed to warm to room temperature over 90 minutes. Water (250 ml) containing sodium carbonate (23 g, 0.22 mol) was added to the suspension and the lower organic layer was separated. This was washed with water (250 ml) containing sodium dihydrogen phosphate (30 g, 0.22 mol). The resulting organic layer was dried over sodium carbonate (anhydrous, 25 g). The solution was filtered and distilled under aspirator pressure (25 Torr). The solvent distilled below room temperature and the product distilled at 96°–102° C. to yield 9.22 g (93%).

NMR (CDCl$_3$): 1.5 (m, 6H, CH$_3$), 2.0 (m, 2H, C—CH$_2$), 4.4 (t, 2H, O—CH$_2$), 8.0 (s, 1H. HCO).

D. Synthesis of 3-isonitrilo-3-methyl-1-butanol

Sodium bicarbonate (8.40 g. 0.10 mol) and sodium carbonate (10.60 g. 0.10 mol) were dissolved in water (200 ml). 3-Isonitrilo-3-methyl-1-butyl formate was added and stirred vigorously. The cloudy solution was allowed to sit for 5 hours at room temperature. Sodium chloride (10 g. 0.17 mol) Was added and the suspension stirred for 15 minutes. The suspension was extracted with ethyl acetate (3×100 ml). The combined organic layers were dried over sodium carbonate (25 g), filtered, and distilled at aspirator pressure (25 Torr). The product distilled at 120° C. to yield 5.38 g (74%).

NMR (CDCl$_3$): 1.5 (m, 6H, CH$_3$), 2.0 (m, 2H, C—CH$_2$), 3.0 (bs, 1H, OH), 4.0 (t, 2H, O—CH$_2$) E. Synthesis of 3-isonitrilo-3-methyl-1-methoxybutane 3 Isonitrilo-3 methyl-1-butanol (1.13 g, 0.01 mol) was dissolved in tetrahydrofuran (20 ml) and dimethylsulfoxide (2 ml). Iodomethane (1.42 g 0.01) was added and the solution stirred at room temperature for 5 minutes. Sodium hydride (80% dispersion in oil, 0.30 g, 0.01 mol) was added in small portions over a 15 minute period. The resulting suspension was stirred for 90 minutes. Water (15 ml) was added and the organic layer separated. The water layer was extracted with ethyl acetate (2×20 ml), and the combined organic layers were dried over sodium carbonate (2 g), filtered, and distilled at aspirator pressure (25 Torr). The product distilled at 80°–90C. to yield 0.48 g (38%).

NMR (CDCl$_3$): 1.5 (m, 6H, CH$_3$), 2.0 (m, 2H, C—CH$_2$), 3.4 (s, 3H, CH$_3$), 3.6 (t, 2H, O—CH$_2$).

Diether-substituted isonitriles useful in the practice of this invention include:

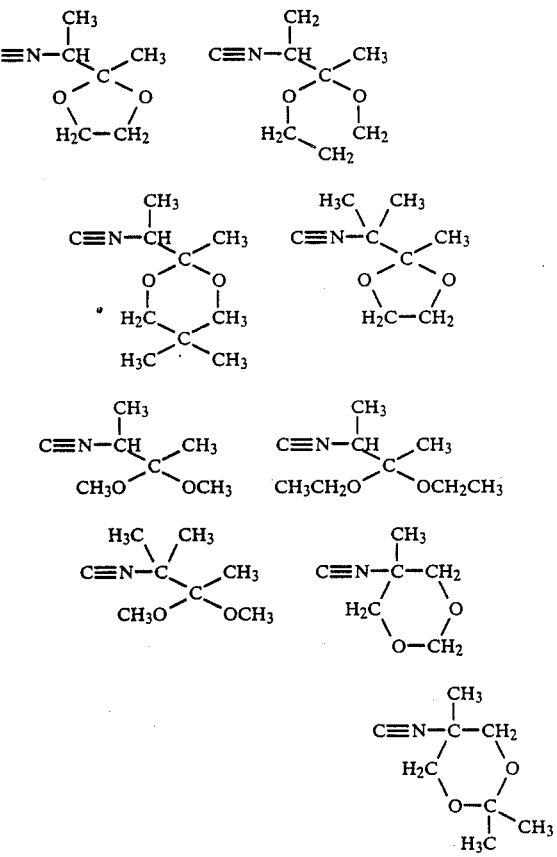

A specific example of the preparation of a diether-substituted isonitrile is set forth below. This procedure is also useful for the preparation of other corresponding diether compounds such as those shown above.

EXAMPLE 4

Preparation of 2-(1-Isonitriloethyl)-2-methyl-1,3-dioxolane

A. Synthesis of 3-Acetamido-2-butanone

From Org. Syn Vol. 4, page 5

Alanine (17.55 g, 0.197 mol) was added to acetic anhydride (119.95 g, 1.176 mol) and pyridine (78.30 g, 0.991 mol). The resulting suspension was heated on a boiling water bath under nitrogen with stirring for 6 hours. The solution was allowed to cool and was distilled under reduced pressure (25 Torr, 35°–40° C.) to remove excess pyridine, acetic anhydride, and acetic acid. The residual oil was transferred to a 100 ml flask equipped with a 10 cm Vigreux column and distilled under reduced pressure (0.5 Torr. 110°–115° C.) to yield slightly impure product (19.39 g, 76%).

NMR (CDCl₃) δ 1.4 (d, 3H, CH-C$\underline{H_3}$), 2.0 (s, 3H, CH₃C(O)CH), 2.2 (s, 3H, C$\underline{H_3}$C(O)(N), 4.6 (p, 1H, CH), 6.9 (bs, 1H, NH).

B. Synthesis of 3-Amino-2-butanone hydrochloride

3-Acetamido-2-butanone (19.39 g, 0.15 mol) was dissolved in 3M HCl (200 ml). The resulting solution was heated at reflux under nitrogen for 6 hours. The solvent was removed by rotary evaporation (25 Torr, 50° C.) and the crude product dried in vacuo (0.5 Torr, 16 hours. 25° C.). The crude product was dissolved in warm ethanol (50 ml). Ether (25 ml) was added and the solution allowed to stand (2° C., 72 hours). The white, crystalline product was filtered and dried in vacuo (0.5 Torr, 16 hours, 25° C.) to yield 12.6 g (68%).

NMR (D₂O) δ 1.3 (d, 3H, C$\underline{H_3}$CH), 2.0 (s, 3H, CH₃CO), 4.0 (q, 1H, CH).

C. Synthesis of 2-(1-Aminoethyl)-2-methyl-1,3-dioxolane hydrochloride

3-Amino-2-butanone hydrochloride (1.24 g, 0.01 mol) was added to toluene (50 ml). Ethylene glycol (0.81 g, 0.013 mol) and p-toluenesulfonic acid (0.17 g, 0.001 mol) were added and the solution was heated to reflux under nitrogen. A Dean-Stark trap was used to collect the water byproduct. When 0.18 ml of water had been collected, the solution was allowed to cool. The solvent was removed by rotary evaporation (25 Torr, 40° C.). The product was dried in vacuo (0.5 Torr 2 hours) to yield 1.3 g (77%) of product contaminated with p-toluenesulfonic acid.

NMR (CD₃OD) δ 1.2 (m, 6H, CH₃CH and CH₃COO), 3.2 (m, 1H, CH), 3.9 (s, 4H, OCH₂CH₂O).

D. Synthesis of 2-(1-Formamidoethyl)-2-methyl-1,3-dioxolane 2-(1-Aminoethyl)-2-methyl-1,3-dioxolane hydrochloride (1.3 g, 0.0078 mol) was dissolved in methanol (25 ml). Sodium methoxide (25% w/w in methanol. 1.68 g, 0.0078 mol) was added and the suspension filtered through Celite. The Celite was rinsed with methanol (25 ml) and the combined filtrates had the solvent removed by rotary evaporation (25 Torr, 40° C.). The resulting clear oil was dissolved in ethyl formate (10.36 g. 0.14 mol) and heated to reflux under nitrogen. The reflux was continued for 4 hours. The excess ethyl formate and ethanol byproduct were removed by rotary evaporation (25 Torr, 40° C.) and the resulting solid was dried in vacuo (0.5 Torr, 25° C., 16 hours). The product was 5 purified using column chromatography on silica gel (20 g. eluant 5% CH₃OH: 95% CH₂Cl₂) to yield 0.80 g (64%).

NMR (CDCl₃) δ 1.2 (d, 3H, CH₃CH), 1.3 (s, 3H, CH₃COO), 3.9 (s, 4H, OCH₂CH₂O),4.3 (m, 1H, CH), 6.1 (b, 1H, NH), 8.0 (s, 1H, HCO).

E. Synthesis of 2-(1-Isonitriloethyl)-2-methyl-1,3-dioxolane 2-(1-Formamidoethyl)-2-methyl-1,3-dioxolane (0.80 g, 0.005 mol) and triethylamine (1.52 g, 0.015 mol) were dissolved in methylene chloride (40 ml) and cooled in an ice/water bath. Trichloromethylchloroformate (0.60 q 0.003 mol) was dissolved in methylene chloride (10 ml) and added dropwise to the stirred, cooled formamide solution. The resulting solution was allowed to slowly warm to room temperature with stirring over 1.5 hours. The solution was added to water (20 ml) containing sodium carbonate (2 g. 0.019 mol) and the layers separated. The organic layer was washed with water (20 ml) containing sodium dihydrogen phosphate (2 g, 0.014 mol). The organic layer was dried over anhydrous sodium carbonate, filtered by gravity through fluted paper, and distilled under reduced pressure (25 Torr). The methylene chloride distilled below room temperature. The product was distilled under reduced pressure (0.5 Torr) at 50° C. to yield 0.25 g (35%).

NMR (CDCl₃) (270 MHz) δ 1.39 (s, 3H, CH₃COO), 1.41 (m, 3H, CH₃CH), 3.68 (m, 1H, CH), 4.04 (m, 4H, OCH₂CH₂O).

The desired radiolabeled, ether-substituted isonitrile complexes are prepared by admixing the isonitrile with the radioactive metal in suitable media at temperatures from room temperature to reflux temperatures or even higher. The desired labeled isonitrile complexes are isolable and can be obtained in high yields. In some cases the isonitrile can itself act as a reducing agent thus eliminating the need for an additional reducing agent. Additional reducing agents, when required or desired to speed up the reaction, are well known to those skilled in the art. Examples of such well-known reducing agents include a stannous salt such as stannous chloride (often used in the form of kits), formamidine sulfinic acid, sodium dithionite, sodium bisulfite, hydroxylamine, ascorbic acid, and the like. The reaction is generally complete after about 1 minute to about 2 hours, depending upon the particular reagents employed and the conditions used.

In the case of technetium such as, for example $^{99}$Tc or $^{99m}$Tc as Tc(I). an isonitrile complex is preferably made by mixing an appropriate reducing agent (capable of reducing technetium in aqueous medium) and the appropriate ether-substituted isonitrile then added pertechnetate. Alternatively, the ether-substituted isonitrile and pertechnetate are mixed, then reductant added.

The isonitrile technetium complexes prepared in accord with this invention can also be prepared from preformed technetium complexes having oxidation states for technetium of, for instance, III, IV or V, by treating these preformed complexes with an excess of ether-substituted isonitrile under suitable conditions.

An excess of the ether-substituted isonitrile, up to 100 fold molar excess or more, and an excess of reducing agent, can be used in the complexing reaction to ensure maximum yield from the technetium. Following the reaction, the desired complex can be separated from the reaction mixture, if required, for example by crystallization or precipitation or by conventional chromatography or ion exchange chromatography; see U.S. Pat. No. 4,452,774, supra, the disclosure of which is hereby incorporated by reference.

Kits in accord with the present invention comprise a sterile, non-pyrogenic, ether-substituted isonitrile ligand and, if required, a quantity of a reducing agent for reducing a preselected radionuclide. Preferably, such kits are sealed. Sterile nonpyrogenic containers (vials) which contain a predetermined quantity of a sterile, ether-substituted isonitrile ligand and a predetermined quantity of a sterile reducing agent such as stannous chloride capable of reducing a predetermined quantity of the preselected radionuclide. It is also preferred that the isonitrile ligand and reducing agent be lyophilized, when possible, to facilitate storage stability. If lyophilization is not practical, the kits can be stored frozen or in solution at room temperature. The ether-substituted isonitrile in such kits can be in the form of a non-radioactive metal adduct such as those described in copending and commonly assigned U.S. Ser. No. 762,392 and in published European Patent Application 183,555, published June 24, 1986. the disclosures of which are hereby incorporated by reference. The displaceable metals useful in the preparation of such metal-adducts are selected from the class consisting of Cu, Mo, Pd, Co, Ni, Cr, Ag, Rh (672,392) and Zn (European 183,555), and can be readily be prepared by admixing a complex of the displaceable metal and the ether-substituted isonitrile ligand in a suitable media at temperatures from room temperature to reflux temperature or even higher. The reaction is generally complete after about 1 minute to about 2 hours, depending upon the reagents employed and the conditions used. The choice of radionuclides will depend on the use. Of course, because of availability of Tc99m generators, such radionuclide is especially preferred.

The following exemplifies the unexpected superiority of the ether-substituted isonitriles of the subject invention over the simple hydrocarbon isonitriles preferred by Jones et al. (U.S. Pat. No. 4,452,774).

EXAMPLE 5

The following Tc99m complexes were prepared:
Complex a: $[^{99m}Tc(C\equiv NC(CH_3)_2CH_2OCH_3)_6]^+$
Complex b: $[^{99m}Tc(C\equiv NCH_2C(CH_3)_2OCH_3)_6]^+$
Complex c: $[^{99m}Tc(C\equiv NCH(CH_3)CH_2OCH_3)_6]^+$
Complex d: $[^{99m}Tc(C\equiv NCH(CH_3)C(OCH_2CH_2O)CH_3)_6]^+$
T-butyl isonitrile complex (comparative):
Complex e: $[^{99m}Tc(C\equiv NC(CH_3)_3)_6]^+$ These technetium complexes were prepared using standard labeling conditions similar to those reported by Jones et al. The isonitrile (3-5 ml) was dissolved in ethanol (1 ml) in a 10 cc serum vial and the vial was sealed and 100-150 mCi of $^{99m}TcO_4^-$ obtained by elution of a $^{99}Mo/^{99m}Tc$ radionuclide generator was added. Sodium dithionite (0.5 ml of a solution of 20-25 mg of 10 ml of distilled water) was added and the vial was placed in a 100° water bath for 15 minutes. After cooling to room temperature, 1 ml of water and 1 ml of methylene chloride were added and the product was extracted into the methylene chloride. The organic layer was evaporated and the product was taken up in ethanol. The purity of the final product was determined by thin layer chromatography on Whatman C-18 reversed-phase plates using a solvent mixture containing 22% 0.5M aqueous ammonium acetate, 66% methanol, 9% acetonitrile, and 3% tetrahydrofuran or high pressure liquid chromatography on a Brownlee C-8 reversed-phase column (5 mm) and a solvent system consisting of 0.05M aqueous ammonium sulfate and methanol with a linear gradient of 0-90% methanol over 20 minutes with a one minute delay from injection.

The complexes were evaluated by determining the biodistribution of each in guinea pigs. Organ distribution of injected activity was determined at 5, 30, and 120 minutes post-injection. For each timepoint, three guinea pigs were anesthetized with sodium pentobarbital (35 mg/kg ip) and injected with 0.1 ml of test material via the jugular vein. The injected dose of $^{99m}Tc$ isonitrile was 1-2.5 mCi. Upon sacrifice, the organs were removed and radioactivity was measured using either a Capintec dose calibrator or gamma well counter. The heart, lungs and liver were weighed. The distribution of radioactivity in the heart, lung, and liver for the complexes are illustrated in the Table below. By reference to the heart/liver and heart/lung ratio, it can readily be seen that the technetium-99m complexes of this invention show marked superiority over the simple hydrocarbon isonitrile complex in exhibiting low uptake by the lungs and lower uptake by the liver (and/or fairly rapid washout from the liver) while maintaining high myocardial uptake.

TABLE

| | % Injected Dose in Heart | | | Organ Ratios | | | | | |
|---|---|---|---|---|---|---|---|---|---|
| | | | | Heart/Lung* | | | Heart/Liver* | | |
| | 5 min | 30 min | 2 hr | 5 min | 30 min | 2 hr | 5 min | 30 min | 2 hr |
| a | 1.7 | 1.2 | 0.8 | 1.5 | 2.9 | 4.8 | 1.6 | 1.6 | 2.7 |
| b | 1.4 | 1.5 | 1.2 | 2.3 | 2.7 | 5.1 | 2.0 | 2.1 | 5.7 |
| c | 1.3 | 1.4 | 0.5 | 3.0 | 3.8 | 2.8 | 2.5 | 5.0 | 3.1 |
| d | 0.9 | 0.8 | 0.6 | 1.6 | 1.8 | 3.6 | 1.2 | 1.4 | 1.7 |
| e | 1.2 | 1.2 | 1.0 | 0.2 | 0.5 | 2.0 | 1.8 | 1.4 | 0.8 |

Note: All values are mean of 3 animals
*Calculated as the ratio of $\frac{\% \text{ injected dose}}{\text{gm. tissue}}$ for each organ a = $[^{99m}Tc(C\equiv NC(CH_3)_2CH_2OCH_3)_6]^+$
b = $[^{99m}Tc(C\equiv NCH_2C(CH_3)_2OCH_3)_6]^+$
c = $[^{99m}Tc(C\equiv NCH(CH_3)CH_2OCH_3)_6]^+$
d = $[^{99m}Tc(C\equiv NCH(CH_3)C(OCH_2CH_2O)CH_3)_6]^+$
e = $[^{99m}Tc(C\equiv NC(CH_3)_3)_6]^+$

What is claimed is:

1. A compound which is an ether-substituted isonitrile of the formula:

$$CN-A-OR \quad \text{or} \quad CN-A-OR$$
$$(I) \qquad\qquad\qquad |$$
$$\qquad\qquad\qquad\qquad OR^1$$
$$\qquad\qquad\qquad\qquad (Ia)$$

wherein
A is a straight or branched chain alkylene group, and
R and $R^1$ each independently is a straight or branched chain alkyl group or taken together are a straight or branched chain alkylene group,
provided that
(1) the total number of carbon atoms in A plus R in formula (I) is 4 to 6, provided further that when the total number of carbon atoms is 6, then the carbon atom alpha to the isonitrile group is a quaternary carbon, and still further provided that A is not $(CH_2)_3$, and
(2) the total number of carbon atoms in A plus R plus $R^1$ in formula (Ia) is 4 to 9.

2. The compound of claim 1 in sterile, non-pyrogenic form.

3. The compound of claim 1 wherein the ether-substituted isonitrile is of formula (Ia) and the total number of carbon atoms in A plus R plus $R^1$ is 4 to 7.

4. The compound of claim 3 wherein the ether substituted isonitrile is $$\begin{array}{c} CH_3 \\ | \\ CN-CH \quad CH_3 \\ \diagdown C \diagup \\ O \quad O \\ \diagdown \quad \diagup \\ CH_2-CH_2 \end{array}$$

5. The compound of claim 3 in sterile, non-pyrogenic form.

6. The compound of claim 1 wherein the ether-substituted isonitrile is of formula (I).

7. The compound of claim 6 wherein the ether-substituted isonitrile is CNCH$_2$C(CH$_3$)$_2$OCH$_3$.

8. The compound of claim 6 wherein the ether-substituted isonitrile is CNC(CH$_3$)$_2$CH$_2$OCH$_3$.

9. The compound of claim 2 wherein the ether-substituted isonitrile is CNCH(CH$_3$)CH$_2$OCH$_3$.

10. The compound of claim 6 wherein the ether-substituted isonitrile is CNCH(CH$_3$)CH$_2$OCH$_2$CH$_3$.

11. The compound of claim 6 wherein the ether-substituted isonitrile is CNCH$_2$CH(CH$_3$)OCH$_3$.

12. The compound of claim 6 wherein the ether-substituted isonitrile is CNCH$_2$CH(CH$_3$)OCH$_2$CH$_3$.

13. The compound of claim 6 wherein the ether-substituted isonitrile is CNCH(CH$_3$)CH(CH$_3$)OCH$_3$.

14. The compound of claim 6 wherein the ether-substituted isonitrile is CNCH$_2$CH(CH$_3$)CH$_2$OCH$_3$.

15. The compound of claim 6 wherein the ether-substituted isonitrile is CNCH$_2$CH$_2$CH(CH$_3$)OCH$_3$.

16. The compound of claim 6 wherein the ether-substituted isonitrile is CNC(CH$_3$)$_2$OCH$_2$CH$_3$.

17. The compound of claim 6 wherein the ether-substituted isonitrile is CNC(CH$_3$)$_2$OCH$_3$.

18. The compound of claim 6 wherein the ether-substituted isonitrile is CN(CH$_2$)$_2$OCH(CH$_3$)$_2$.

19. The compound of claim 6 wherein the ether-substituted isonitrile is CN(CH$_2$)$_2$OCH$_2$CH$_3$.

20. The compound of claim 6 wherein the ether-substituted isonitrile is CNCH$_2$CH(CH$_2$CH$_3$)OCH$_3$.

21. The compound of claim 6 wherein the ether-substituted isonitrile is CNCH(CH$_2$CH$_3$)CH$_2$OCH$_3$.

22. The compound of claim 6 wherein the ether-substituted isonitrile is CNCHCH$_3$OCH(CH$_3$)$_2$.

23. The compound of claim 6 wherein the ether-substituted isonitrile is CNCH(CH$_3$)CH$_2$CH$_2$OCH$_3$.

24. The compound of claim 6 wherein the ether-substituted isonitrile is CNC(CH$_3$)CH$_2$CH$_2$OCH$_3$.

25. The compound of claim 6 in sterile, non-pyrogenic form.

26. The compound of any of claims 8 and 9 through 24 in sterile, non-pyrogenic form.

* * * * *